(12) United States Patent
Ohmae

(10) Patent No.: US 8,864,030 B2
(45) Date of Patent: Oct. 21, 2014

(54) SAMPLE ANALYZER, METHOD OF OBTAINING SAMPLE IDENTIFICATION INFORMATION AND SAMPLE IDENTIFICATION INFORMATION OBTAINING APPARATUS

(75) Inventor: Yuichiro Ohmae, Kobe (JP)

(73) Assignee: Sysmex Corporation, Kobe (JP)

( * ) Notice: Subject to any disclaimer, the term of this patent is extended or adjusted under 35 U.S.C. 154(b) by 65 days.

(21) Appl. No.: 13/039,977

(22) Filed: Mar. 3, 2011

(65) Prior Publication Data

US 2011/0215149 A1 Sep. 8, 2011

(30) Foreign Application Priority Data

Mar. 5, 2010 (JP) .................... 2010-048593

(51) Int. Cl.
*G06K 7/10* (2006.01)
*G01N 35/00* (2006.01)

(52) U.S. Cl.
CPC ............ *G01N 35/00732* (2013.01); *G01N 2035/00752* (2013.01)
USPC ........... 235/462.01; 422/62; 422/64; 422/65

(58) Field of Classification Search
CPC .............. B01J 19/0006; B01J 19/0046; B01J 2219/0059; B01J 2219/00596; C40B 60/14; G01N 35/025; G01N 35/00029; G01N 2035/00752; G01N 21/253; G01N 35/1002; G01N 35/026; G01N 35/04; G01N 35/021; G06K 7/14; G06K 7/10851; G06K 7/10881; G02B 26/10

USPC ............. 235/462.01, 462.013; 422/62, 64, 65
See application file for complete search history.

(56) References Cited

U.S. PATENT DOCUMENTS

2004/0060492 A1* 4/2004 Okazaki et al. ............... 112/63
2010/0240063 A1* 9/2010 Hayes et al. .................. 435/6

FOREIGN PATENT DOCUMENTS

| JP | 60104955 A | 7/1985 |
|---|---|---|
| JP | 04-063065 U | 5/1992 |
| JP | 09-089902 A | 4/1997 |
| JP | 2004-028963 A | 1/2004 |
| JP | 2004-226065 A | 8/2004 |

* cited by examiner

Primary Examiner — Thien M Le
Assistant Examiner — Asifa Habib
(74) Attorney, Agent, or Firm — Brinks Gilson & Lione

(57) ABSTRACT

A sample analyzer comprising: a measurement unit for measuring a sample contained in a sample container; a barcode reader; a rotating section; and a controller is disclosed. The controller controls the rotating section and the barcode reader so that the barcode reader repeatedly reads the barcode over the range of a predetermined rotation angle; and obtains identification information of the sample contained in the sample container on the basis of reading results obtained as a result of the repeated reading of the barcode by the barcode reader. Method of obtaining sample identification information and a sample identification information obtaining apparatus are also disclosed.

16 Claims, 14 Drawing Sheets

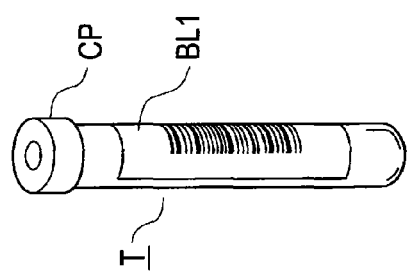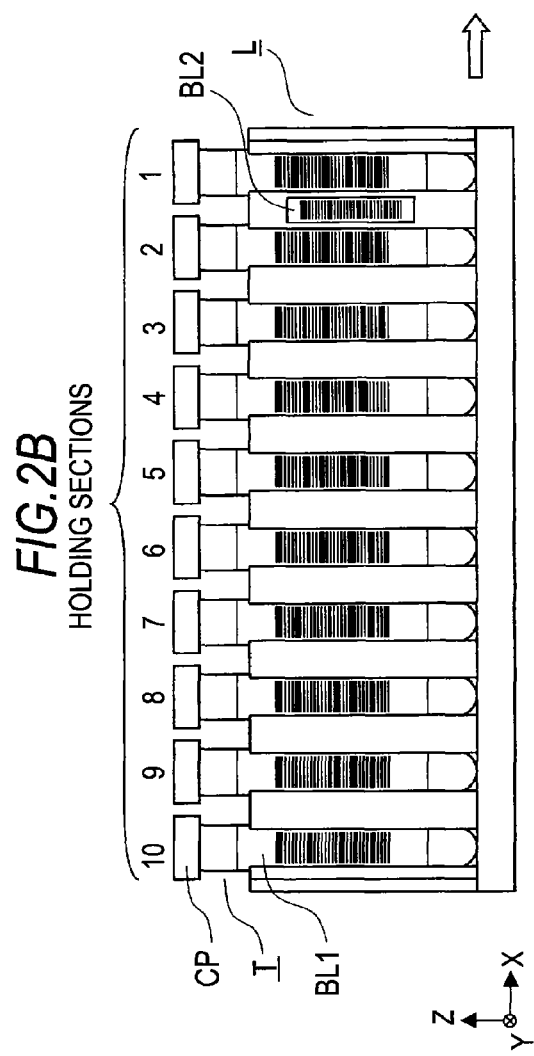

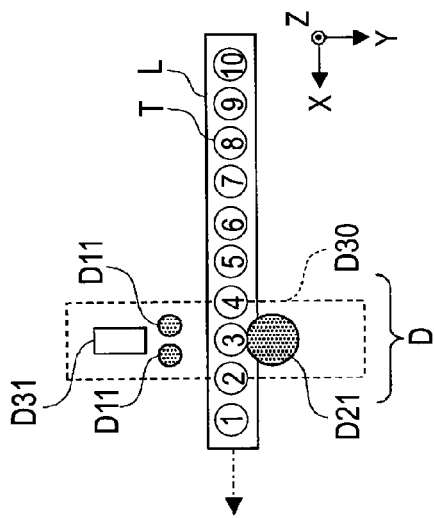
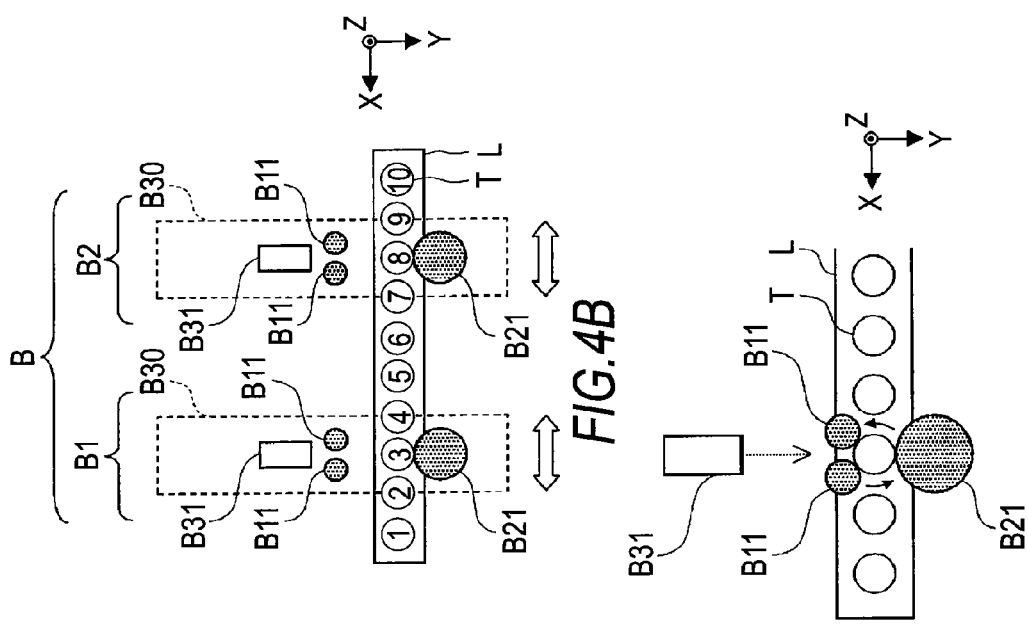

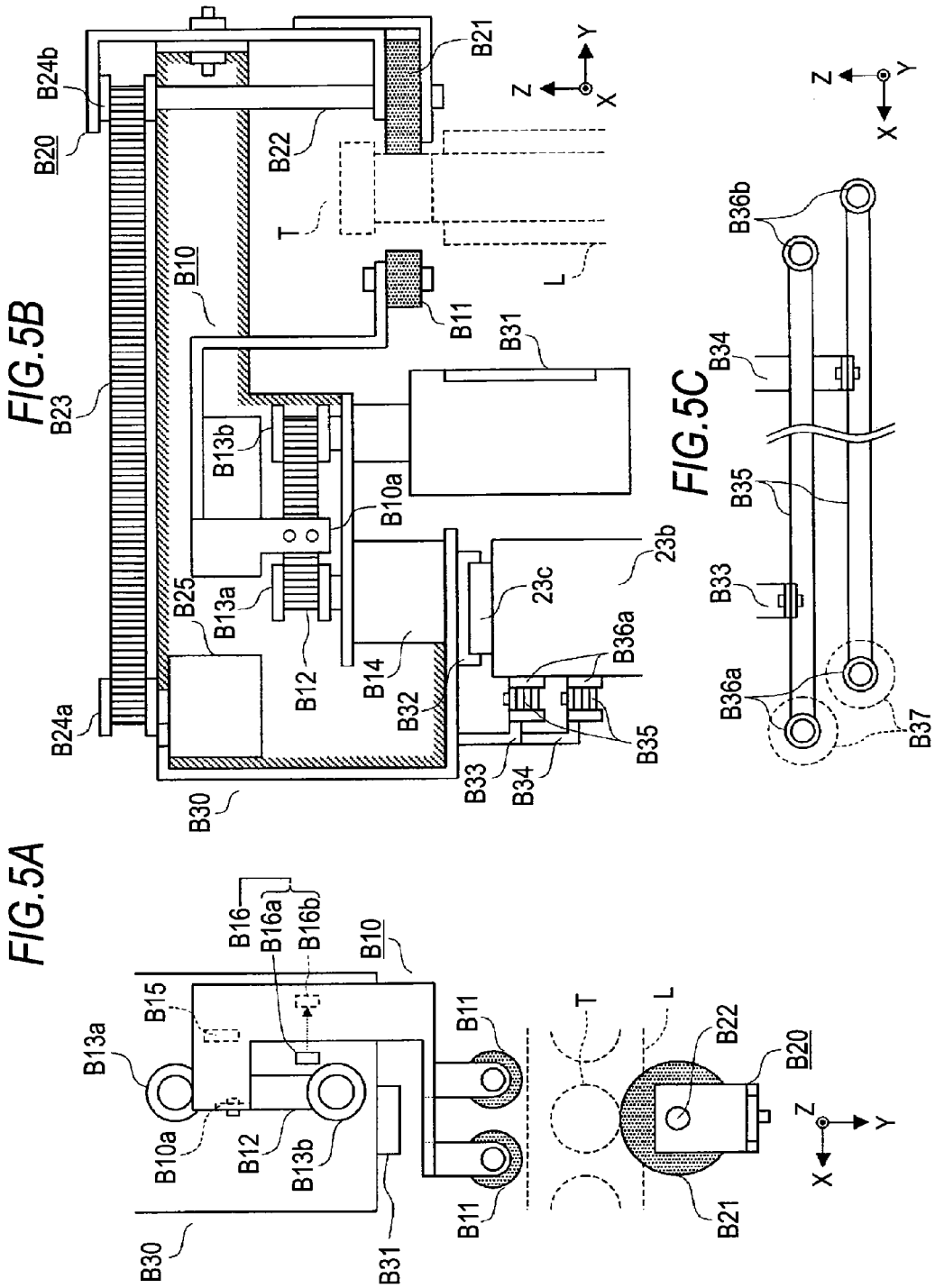

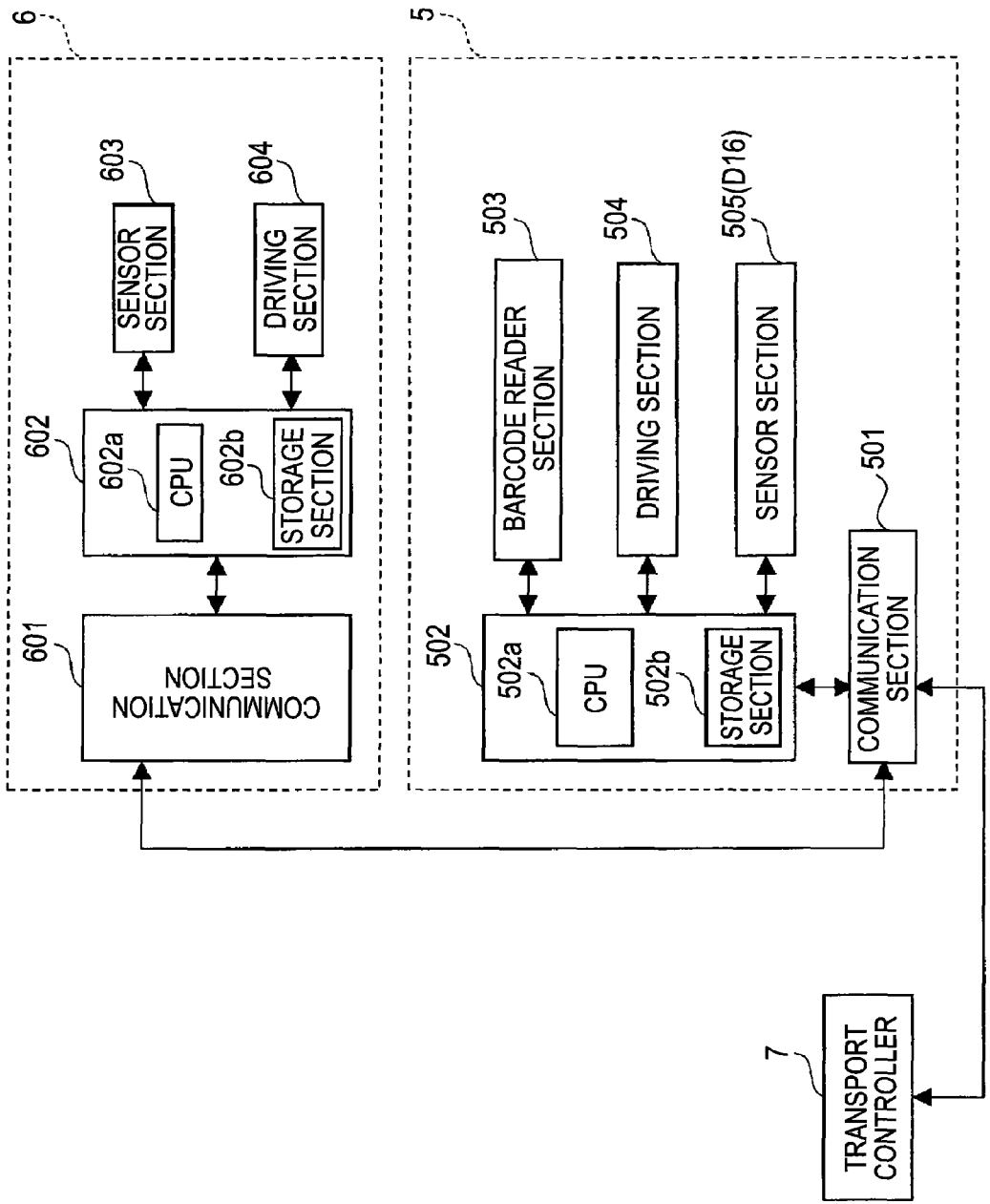

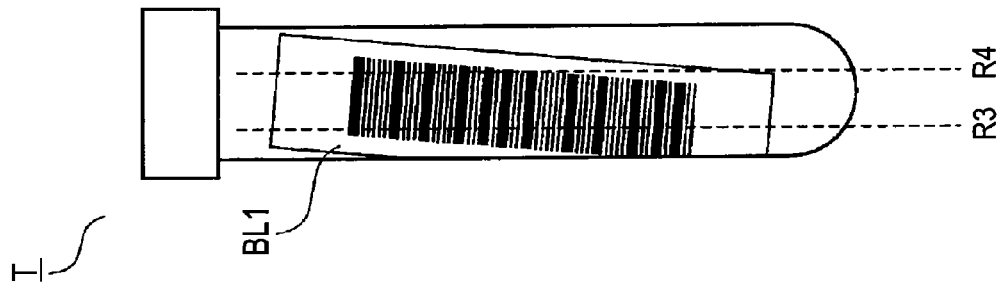
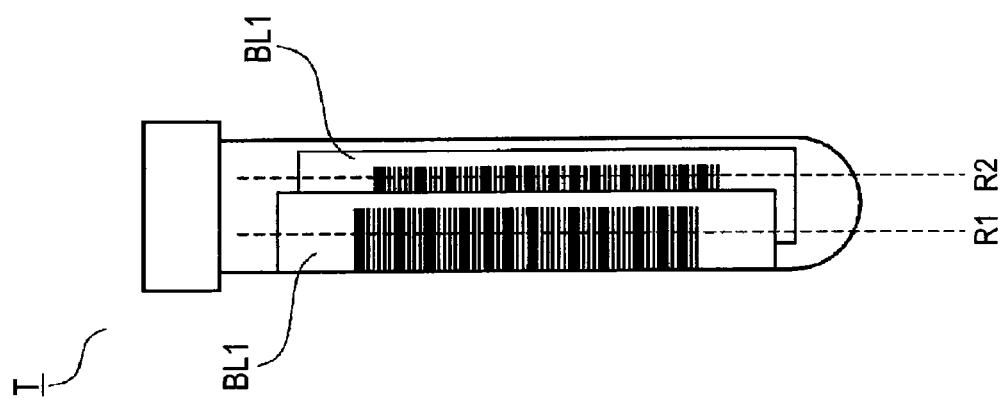

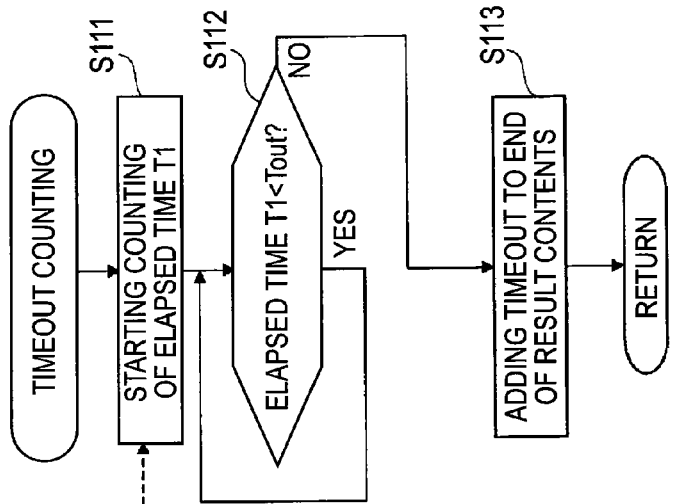
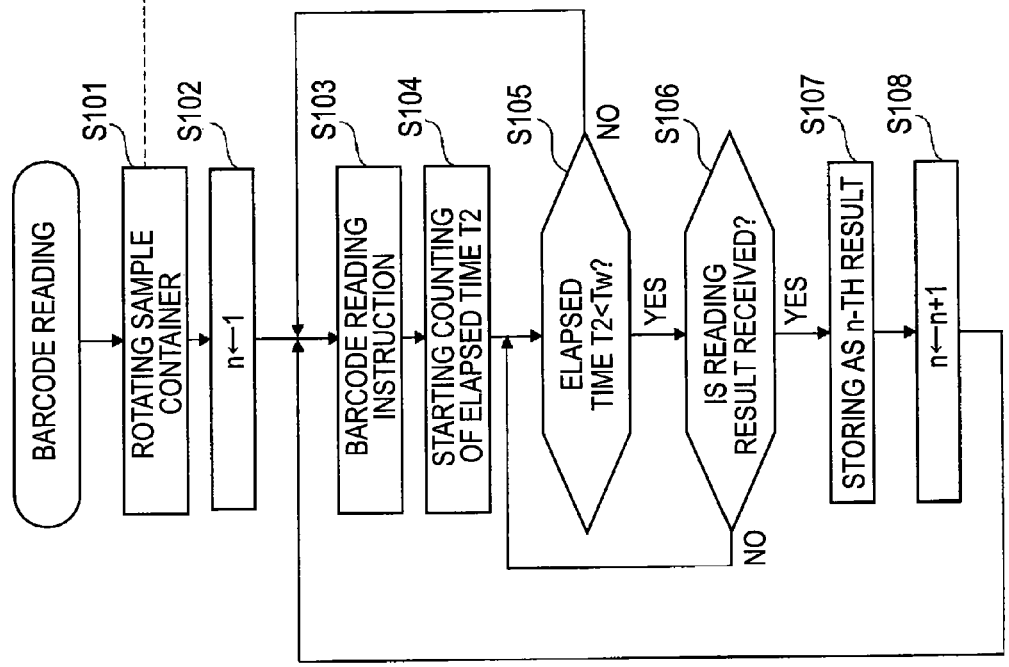

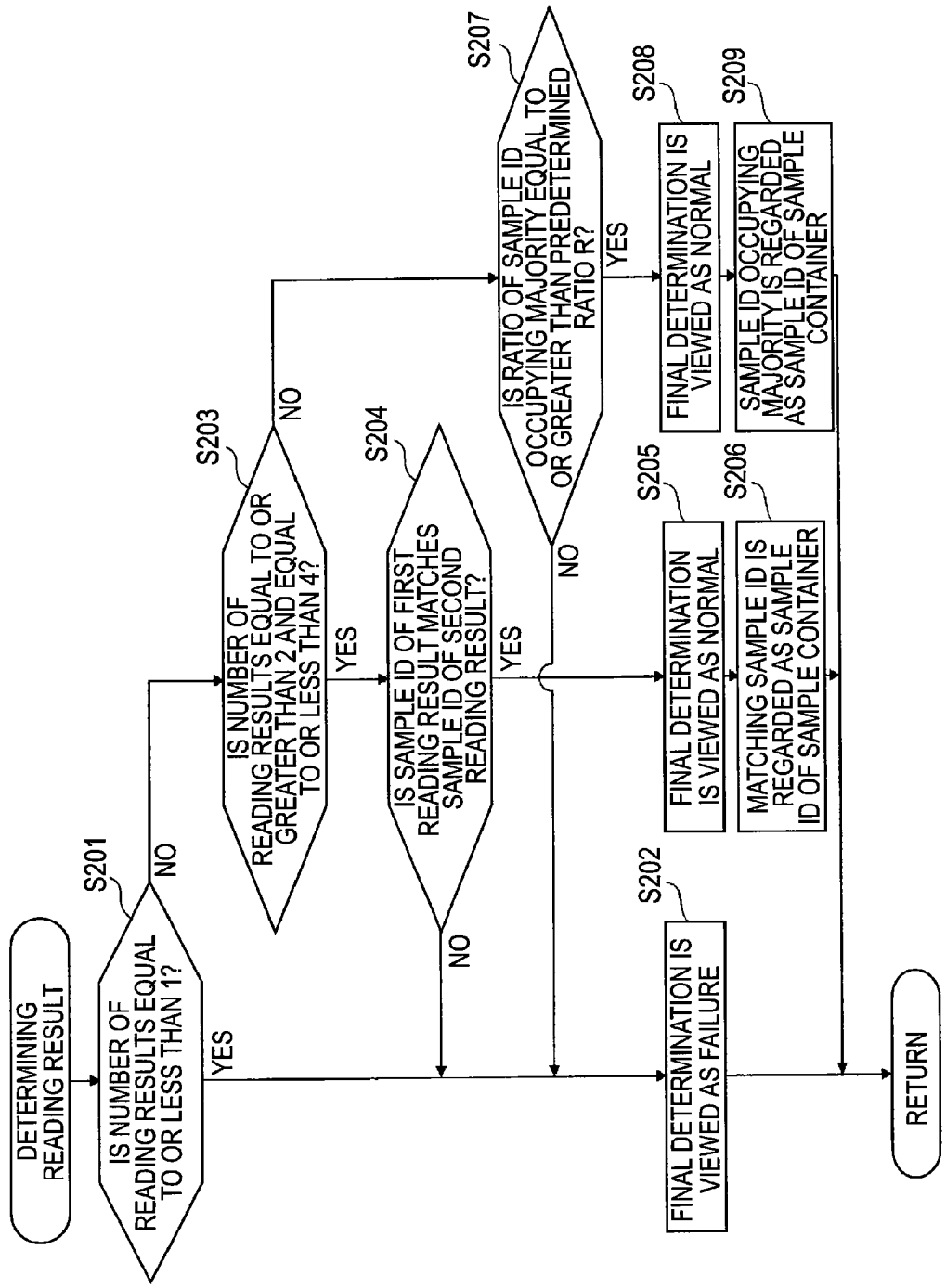

FIG.13

| SAMPLE NO. | READING RESULTS | | | | | | | | FINAL DATA | | FINAL DETERMINATION |
|---|---|---|---|---|---|---|---|---|---|---|---|
| | FIRST | SECOND | THIRD | FOURTH | FIFTH | ... | n-TH | ... | NUMBER OF DATA | RATIO | |
| 1 | T/O | — | — | — | — | — | — | — | 0/0 | 0% | FAILURE |
| 2 | 'AAA' | T/O | — | — | — | — | — | — | 1/1 | 100% | FAILURE |
| 3 | 'AAA' | 'AAA' | T/O | — | — | — | — | — | 2/2 | 100% | NORMAL |
| 4 | 'AAA' | 'AAA' | 'AAA' | 'AAA' | — | — | — | — | 4/4 | 100% | NORMAL |
| 5 | 'AAA' | 'AAA' | 'AAA' | 'BBB' | T/O | — | — | — | 3/4 | 75% | NORMAL |
| 6 | 'AAA' | 'BBB' | 'AAA' | 'AAA' | T/O | — | — | — | 3/4 | 75% | FAILURE |
| 7 | 'AAA' | 'BBB' | NG | 'AAA' | T/O | — | — | — | 4/5 | 80% | NORMAL |
| 8 | 'AAA' | 'AAA' | 'AAA' | 'BBB' | 'AAA' | 'BBB' | T/O | — | 3/6 | 50% | FAILURE |
| 9 | 'AAA' | 'AAA' | 'BBB' | 'CCC' | 'AAA' | ... | 'AAA' | T/O | x/n | > 60% | NORMAL |
| 10 | 'AAA' | 'AAA' | 'BBB' | 'CCC' | 'AAA' | ... | 'AAA' | T/O | x/n | < 60% | FAILURE |

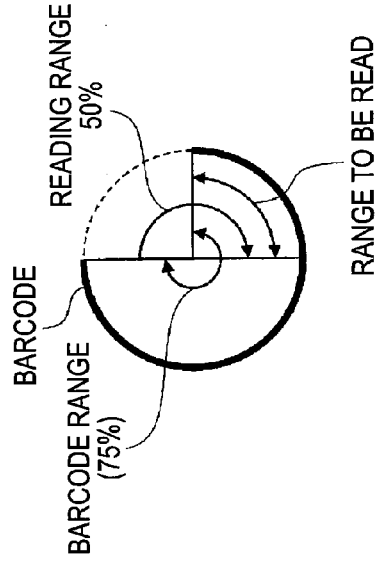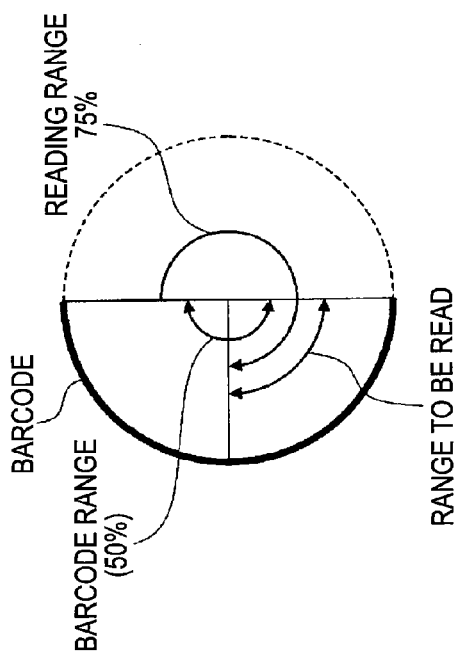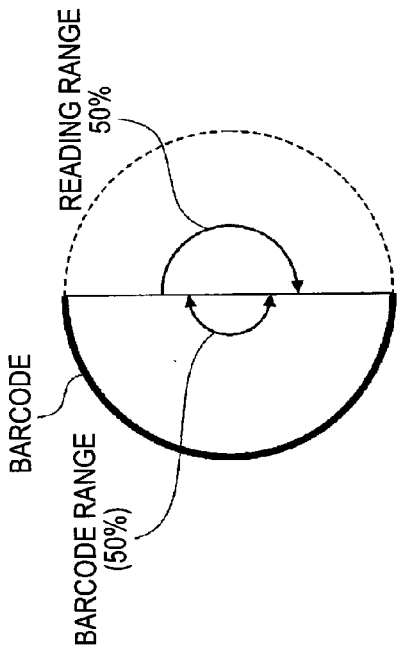

SAMPLE ANALYZER, METHOD OF OBTAINING SAMPLE IDENTIFICATION INFORMATION AND SAMPLE IDENTIFICATION INFORMATION OBTAINING APPARATUS

RELATED APPLICATIONS

This application claims priority under 35 U.S.C. §119 to Japanese Patent Application No. 2010-048593 filed on Mar. 5, 2010, the entire content of which is hereby incorporated by reference.

BACKGROUND OF THE INVENTION

1. Field of the Invention

The present invention relates to a sample analyzer which analyzes a sample contained in a sample container, a method of obtaining sample identification information to obtain identification information of a sample contained in a sample container by reading a barcode adhered to the sample container, and a sample identification information obtaining apparatus.

2. Description of the Related Art

Currently, sample analyzers for processing clinical samples such as blood or urine are being used in medical centers. In this kind of sample analyzer, a configuration for obtaining identification information of a sample contained in a sample container by reading a barcode adhered to the sample container is provided.

In the automatic hemanalysis device described in JP laid-open patent application H09-89902, the barcode adhered to a sample is read while a sample container is rotated. Here, after the start of the reading, when barcode information which matches three times in succession is obtained, the identification information of the sample is obtained on the basis of this barcode information.

A sample container may be moved from a medical center to another medical center. In this case, the identification information of a sample is newly assigned in the medical center after the transfer. A new barcode is issued on the basis of the newly assigned identification information and is adhered to the sample container. At this time, the new barcode is adhered over the barcode which is adhered in the medical center before the transfer. When misalignment occurs between the new barcode and the old barcode when the new barcode is adhered, the old barcode is partially exposed to the outside.

In this case, in the device in JP laid-open patent application H09-89902, when the reading is started from the old barcode, the barcode information based on the old barcode is read three times in succession, and on the basis of this barcode information, wrong identification information may be obtained.

SUMMARY OF THE INVENTION

A first aspect of the present invention is a sample analyzer comprising: a measurement unit for measuring a sample contained in a sample container; a barcode reader for reading a barcode adhered to the sample container by irradiating a side surface of the sample container with light; a rotating section for rotating the sample container relative to the barcode reader so that a position at which the reading is performed by the barcode reader moves in a circumferential direction of the sample container; and a controller which executes operations, the operations comprising: controlling the rotating section and the barcode reader so that the barcode reader repeatedly reads the barcode over the range of a predetermined rotation angle; and obtaining identification information of the sample contained in the sample container on the basis of reading results obtained as a result of the repeated reading of the barcode by the barcode reader.

A second aspect of the present invention is a sample analyzer comprising: a measurement unit for measuring a sample contained in a sample container; a barcode reader for reading a barcode adhered to the sample container by irradiating a side surface of the sample container with light; a rotating section for rotating the sample container relative to the barcode reader so that a position at which the reading is performed by the barcode reader moves in a circumferential direction of the sample container; and a controller, wherein the controller performs a rotating process of rotating the sample container until the sample container rotates a predetermined angle by the rotating section while repeatedly performing a reading process of reading the barcode by the barcode reader; and the controller obtains identification information of the sample contained in the sample container on the basis of reading results obtained by the repeated reading processes.

A third aspect of the present invention is method of obtaining sample identification information, the method comprising: repeatedly reading a barcode adhered to a sample container over a range of a predetermined rotation angle by rotating the sample container; and obtaining identification information of a sample contained in the sample container on the basis of reading results obtained as a result of the repeated reading of the barcode.

A fourth aspect of the present invention is a sample identification information obtaining apparatus comprising: a barcode reader for reading a barcode adhered to the sample container by irradiating a side surface of the sample container with light; a rotating section for rotating the sample container relative to the barcode reader so that a position at which the reading is performed by the barcode reader moves in a circumferential direction of the sample container; and a controller which executes operations, the operations comprising: controlling the rotating section and the barcode reader so that the barcode reader repeatedly reads the barcode over the range of a predetermined rotation angle; and obtaining identification information of the sample contained in the sample container on the basis of reading results obtained as a result of repeated reading of the barcode by the barcode reader.

BRIEF DESCRIPTION OF THE DRAWINGS

FIGS. 2A and 2B show configurations of a sample container and a sample rack according to the embodiment.

FIGS. 4A to 4D show plan views schematically showing the configuration of a barcode unit according to the embodiment.

FIGS. 5A to 5C show the configuration of the barcode unit according to the embodiment in detail.

FIG. 8 is a diagram showing the functional configurations of a sample transport unit and a smear preparation apparatus according to the embodiment.

FIGS. 9A and 9B show the state in which on an old barcode label which is adhered to a sample container, another new barcode label is adhered, and the state in which a barcode label which is adhered to a sample container is slanted.

FIGS. 11A and 11B show flowcharts showing a barcode reading process and a timeout counting process according to the embodiment.

FIG. 12 is a flowchart showing a reading result determination process according to the embodiment.

FIG. 13 is a table showing examples of reading results, final data and final determination according to the embodiment.

FIGS. 14A to 14C schematically show a ratio of a barcode range to the outer circumference of a sample container T and a ratio of a reading range of a barcode reader according to the embodiment.

DETAILED DESCRIPTION OF THE PREFERRED EMBODIMENTS

Hereinafter, a sample analysis system according to an embodiment of the present invention is described referring to the accompanied drawings. However, the scope of the present invention is not necessarily limited to the embodiment described below.

This embodiment is a sample analysis system for examination and analysis related to blood, to which the invention is applied. A sample analysis system according to this embodiment includes three measurement units and one smear preparation apparatus. In the three measurement units, blood analysis is performed concurrently, and when it is necessary to prepare a smear based on the analysis result thereof, the smear preparation apparatus prepares a smear.

Hereinafter, a sample analysis system according to this embodiment will be described with reference to the drawings.

Figure 1:
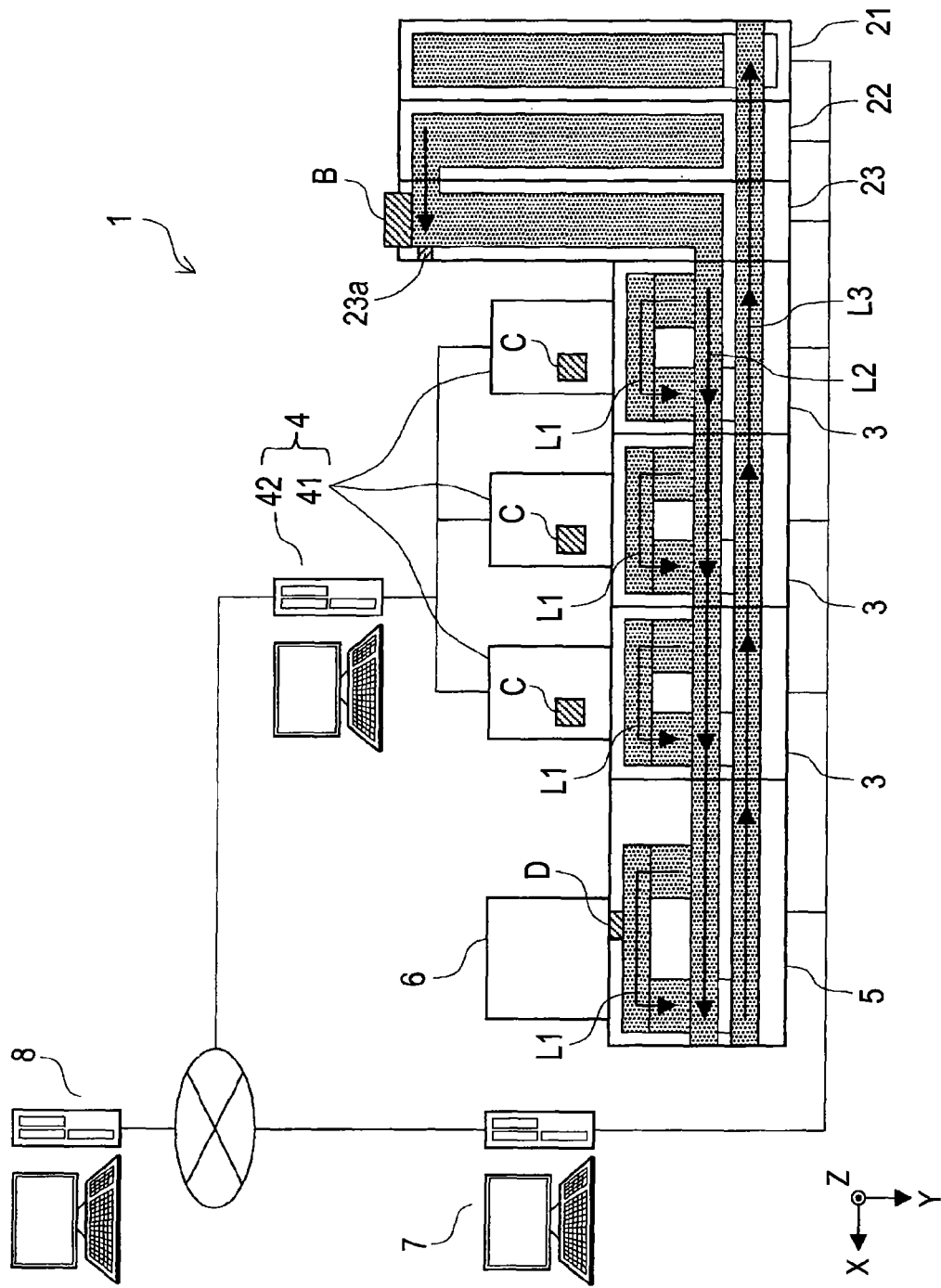
FIG. 1 is a plan view schematically showing the configuration of a sample analysis system according to an embodiment.

FIG. 1 is a plan view schematically showing the configuration when a sample analysis system 1 is viewed from the upper side. The sample analysis system 1 according to this embodiment is configured to include a sample recovery unit 21, a sample insertion unit 22, a sample output unit 23, three sample transport units 3, a blood cell analysis apparatus 4, a sample transport unit 5, a smear preparation apparatus 6, and a transport controller 7. In addition, the sample analysis system 1 of this embodiment is connected to a host computer 8 via a communication network so as to communicate therewith.

Each of the sample recovery unit 21, the sample insertion unit 22, and the sample output unit 23 is configured so that a plurality of sample racks can be placed therein.

FIG. 2 shows the configurations of a sample container T and a sample rack L. FIG. 2A is a perspective view showing the appearance of a sample container T and FIG. 2B is a front view of a sample rack L.

Referring to FIG. 2A, a sample container T is a tubular container (vacuum blood collection tube) made of glass or a synthetic resin having translucency. The upper end of the container is opened and the opening is sealed by a cap section CP. A barcode label BL1 is adhered to a side surface of the sample container T. On the barcode label BL1, a barcode showing a sample ID is printed. In the sample container T, a blood sample collected from a patient is contained and the opening of the upper end is sealed by the cap section CP. In the cap section CP, a hole is formed in the vertical direction so that a pipette passes therethrough.

Referring to FIG. 2B, in a sample rack L, ten holding sections are formed so as to arrange and hold ten sample containers T in a vertical state (erect state). In addition, as shown in FIG. 2B, a barcode label BL2 is adhered to a surface (surface in the Y-axis negative direction) on the inward side when the sample rack L is set in the sample insertion unit 22. On the barcode label BL2, a barcode showing a rack ID is printed.

Returning to FIG. 1, the sample recovery unit 21 stores sample racks L in which analysis has ended. The sample insertion unit 22 stores sample racks L which are inserted by a user and outputs the stored sample racks L toward the sample output unit 23 from the innermost position (end in the Y-axis negative direction) in the leftward direction (in the X-axis positive direction). In addition, the sample recovery unit 21 and the sample insertion unit 22 are connected to the transport controller 7 so as to communicate therewith.

As shown in FIG. 1, the sample output unit 23 has a sensor 23a which is installed on the left side of the innermost position and a barcode unit B which is installed on the innermost side. The sensor 23a detects a sample rack L output from the sample insertion unit 22 and positioned on the innermost side of the sample output unit 23. The barcode unit B reads a rack ID of the sample rack L positioned on the innermost side and a sample ID of a sample container T held in this sample rack L.

In addition, the sample output unit 23 outputs a sample rack L in which the reading of the barcode has been completed to the sample transport unit 3. Further, the sample output unit 23 is connected to the transport controller 7 so as to communicate therewith and the rack ID and the sample ID read by the sample output unit 23 are transmitted to the transport controller 7. The configuration of the barcode unit B will be described later with reference to FIG. 4.

The three sample transport units 3 are disposed in front of three measurement units 41 (in the Y-axis positive direction), respectively, as shown in FIG. 1. The neighboring two sample transport units 3 are connected to each other so as to deliver sample racks L. The right end of the sample transport unit 3 on the right side (X-axis negative direction) is connected to the sample output unit 23 so as to deliver sample racks L, and the left end of the sample transport unit 3 on the left side (in the X-axis positive direction) is connected to the sample transport unit 5 so as to deliver sample racks L. In addition, the three sample transport units 3 are respectively connected to an information processing unit 42 and the transport controller 7 so as to communicate therewith.

As shown in FIG. 1, in these three sample transport units 3, two transport lines L1 and L2 for transporting the sample racks L are set by dividing cases into the cases in which the measurement of a sample is performed in the respective corresponding measurement units 41 and the cases in which the measurement is not performed. That is, when the measurement of a sample is performed by the measurement unit 41, a sample rack L is transported along the transport line L1 shown by the U-shaped rear arrow. When the measurement of a sample is not performed in the measurement unit 41, a sample rack L is transported along the transport line L2 shown by the intermediate left-pointing arrow so as to skip the present measurement unit 41.

Further, in the three sample transport units 3, a transport line L3 for transporting the sample racks L to the sample recovery unit 21 is set as shown in FIG. 1. That is, a sample rack L, in which measurement has ended or preparation of a smear has ended, is transported along the transport line L3 shown by the front (in the Y-axis positive direction) rightpointing (in the X-axis negative direction) arrow and is recovered by the sample recovery unit 21.

The blood cell analysis apparatus 4 is an optical flow cytometry type multiple blood cell analysis apparatus and includes the three measurement units 41 and the information processing apparatus 42. Each of the three measurement units 41 has a barcode unit C and measures a blood sample which is contained in a sample container T. The information processing unit 42 is connected to the three measurement units 41 so as to communicate therewith and control the operations of the three measurement units 41. In addition, the information processing unit 42 is also connected to the three sample transport units 3 so as to communicate therewith.

Here, referring to FIG. 3, the measurement operation in the measurement unit 41 will be described.

Figure 3:
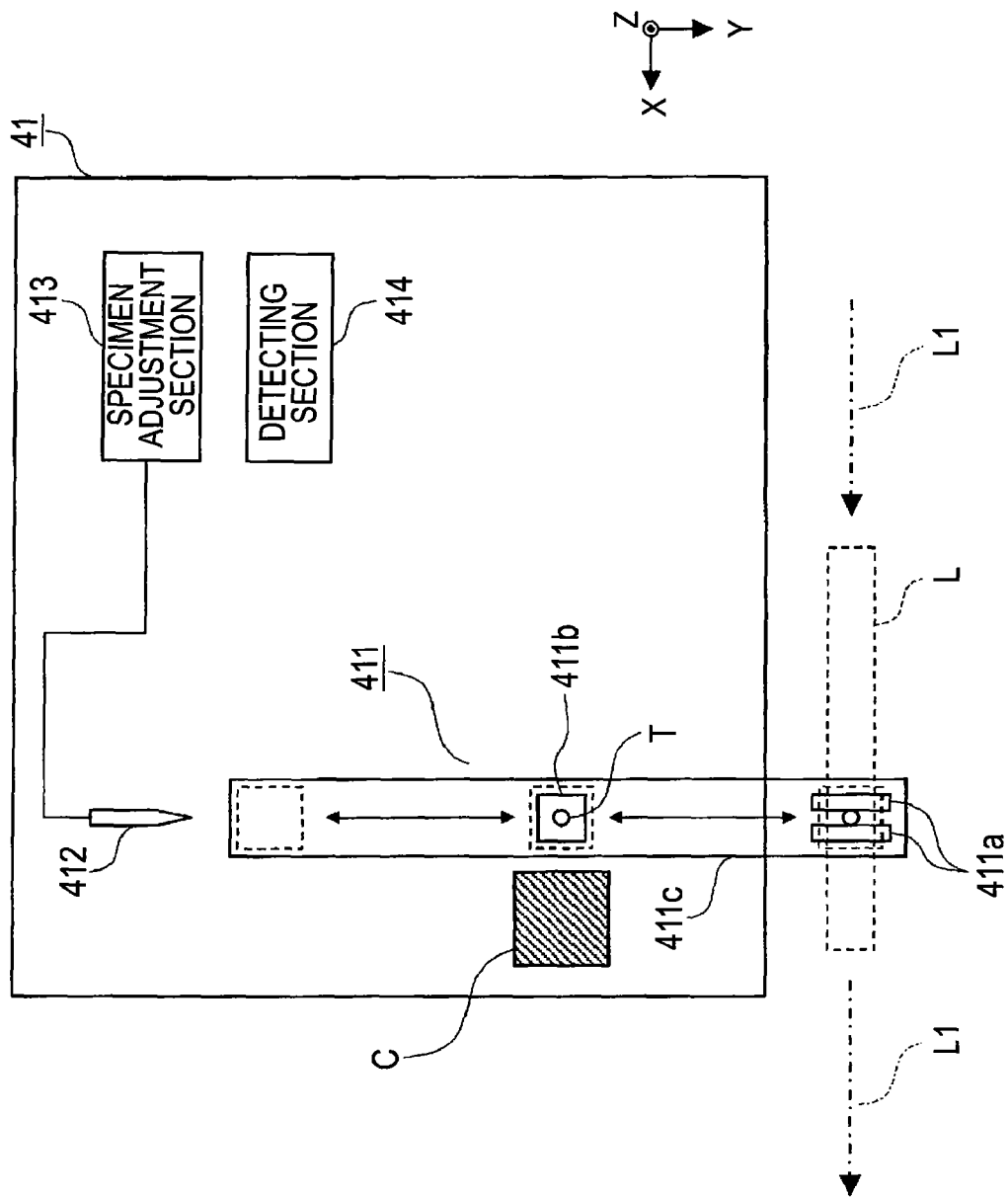
FIG. 3 is a plan view schematically showing the configuration of a measurement unit according to the embodiment.

FIG. 3 is a plan view schematically showing the configuration when the measurement unit 41 is viewed from the upper side. First, a hand section 411a installed at the front end of a sample container transport section 411 grips a sample container T which is held in a sample rack L at a predetermined position on the transport line L1 and takes it upward (in the Z-axis positive direction). The taken sample container T is stirred by the hand section 411a and then set in a sample container setting section 411b.

The sample container setting section 411b is configured to be moved in the Y-axis direction by a transport mechanism section 411c. The transport mechanism section 411c includes a belt, two pulleys, and a stepping motor (not shown).

The sample container T set in the sample container setting section 411b is positioned in front of the barcode unit C (in the X-axis negative direction) due to the backward movement (Y-axis negative direction) of the sample container setting section 411b. In this state, the barcode unit C reads a sample ID of the sample container T. Such a sample ID is transmitted to the information processing unit 42. The configuration of the barcode unit C will be described later with reference to FIG. 4.

On the basis of the received sample ID, the information processing unit 42 inquires of the host computer 8 for a measurement order. On the basis of the result of such inquiry, the measurement of the sample which is contained in the sample container T is instructed by the information processing unit 42.

Next, the sample container T is positioned under a sample suction section 412 (in the Z-axis negative direction) due to the backward movement of the sample container setting section 411b. The sample suction section 412 suctions the sample in the sample container T which is positioned under the sample suction section 412. After that, the sample container T returns along the original course and returns to the original holding position in the sample rack L.

A specimen adjustment section 413 has a plurality of reaction chambers (not shown). The specimen adjustment section 413 mixes and stirs a reagent and the sample suctioned by the sample suction section 412 in a reaction chamber and prepares a specimen for measurement. A detecting section 414 measures the specimen prepared by the specimen adjustment section 413. The measurement data obtained by such measurement is analyzed by the information processing unit 42.

Returning to FIG. 1, the sample transport unit 5 is disposed in front of the smear preparation apparatus 6 (in the Y-axis positive direction). As in the sample transport unit 3, in the sample transport unit 5, transport lines L1, L2 and L3 are set. In addition, the sample transport unit 5 is connected to the transport controller 7 so as to communicate therewith. Further, the sample transport unit 5 is connected to the smear preparation apparatus 6, and in accordance with an instruction from the sample transport unit 5, the smear preparation apparatus 6 is driven.

In addition, the sample transport unit 5 has a barcode unit D near the transport line L1. The barcode unit D reads the rack ID of a sample rack L positioned in front of the barcode unit D and a sample ID of a sample container T associated with the holding section in the sample rack L. The configuration of the barcode unit D will be described later with reference to FIG. 4.

In addition, the sample transport unit 5 has a transport mechanism for transporting a sample rack L along the transport line L1. This transport mechanism includes a belt, two pulleys, and a stepping motor (not shown) in order to transport a sample rack L in the right- and leftward directions (in the X-axis direction) immediately in front of the smear preparation apparatus 6 (in the Y-axis positive direction).

In the smear preparation apparatus 6, a smear of a blood sample is prepared. That is, first, the smear preparation apparatus 6 suctions a blood sample contained in a sample container T at a predetermined position on the transport line L1 of the sample transport unit 5. Next, the suctioned blood sample is dropped onto a glass slide, thinly extended on the glass slide, and then is dried. After that, a liquid dye is supplied to the glass slide to dye the blood on the glass slide and a smear is prepared.

Whether the preparation of a smear is required is determined by the transport controller 7 on the basis of the result of the analysis which is performed by the information processing unit 42, based on the result of the measurement in the three measurement units 41. The result of the analysis which is performed by the information processing unit 42 is transmitted to the transport controller 7 via the sample transport unit 3. When the transport controller 7 determines that the preparation of a smear is required, the sample rack L storing a target sample is transported along the transport line L1 of the sample transport unit 5 and a smear is prepared in the smear preparation apparatus 6.

The transport controller 7 is connected to the sample recovery unit 21, the sample insertion unit 22, the sample output unit 23, the three sample transport units 3, and the sample transport unit 5 so as to communicate therewith and controls the driving of each unit. As the transport controller 7, for example, a separate personal computer or a computer incorporated in the system is used.

When receiving the rack ID of a sample rack L, the sample ID of a sample container T and the holding position of the sample container T from the sample output unit 23, the transport controller 7 inquires of the host computer 8 for a measurement order. When receiving a measurement order from the host computer 8, the transport controller 7 stores the measurement order in association with the rack ID, the sample ID and the holding position.

In addition, the transport controller 7 determines whether a sample rack L which is output from the sample output unit 23 is transported to any of the three measurement units 41. The transport controller 7 transmits the stored measurement order to the sample transport unit 3 in front of the measurement unit 41 which is determined as a transport destination. The transport controller 7 controls each sample transport unit 3 so as to transport this sample rack L up to the measurement unit 41 which is determined as a transport destination.

The host computer 8 is connected to the communication network and can communicate with the information processing unit 42 and the transport controller 7. In a storage section of the host computer 8, measurement orders are stored. When the information processing unit 42 or the transport controller 7 requests a measurement order including a sample ID, the host computer 8 reads out the measurement order corresponding to this sample ID from the storage section and transmits the measurement order to the information processing unit 42 or the transport controller 7.

FIG. 4 shows plan views schematically showing the configurations when the barcode units A, B and C are viewed from the upper side, respectively.

FIG. 4A is a view showing the barcode unit B. As shown in FIG. 4A, the barcode unit B has two reading sections B1 and B2 which are juxtaposed in the horizontal direction (in the X-axis direction). Each of the reading sections B1 and B2 includes two rollers B11, a roller B21, a base B30, and a barcode reader B31.

In the reading sections B1 and B2, the two rollers B11 are configured to rotate around the Z-axis and to be moved in the Y-axis direction on the base B30. The roller B21 is configured to rotate and be driven around the Z-axis and is fixed on the base B30. The barcode reader B31 is fixed to the base B30 and reads a barcode which is positioned immediately ahead thereof (in the Y-axis positive direction). On the innermost side of the sample output unit 23, the base B30 is configured to be moved in the horizontal direction. A mechanism for driving the rollers B11 and B21 and the base B30 is disposed on the innermost side of the sample output unit 23 (inward side of the sample rack L in FIG. 4A).

When the barcode reader B31 reads the sample ID of a sample container T which is positioned immediately ahead thereof, the two rollers B11 are moved forward (in the Y-axis positive direction) so as to be brought into contact with the side surface of the sample container T as shown in FIG. 4B. At this time, the side surface of the sample container T on the nearest side is brought into contact with the roller B21. In this state, due to the rotation and the driving of the roller B21, the sample container T is rotated around the Z-axis and the barcode label BL1 is read multiple times by the barcode reader B31 during the rotation of the sample container T. When the barcode reader B31 reads the barcode label BL2 (see FIG. 2B), which is adhered between the holding sections 1 and 2 in the sample rack L, the rollers B11 are not driven forward.

When a sample rack L output from the sample insertion unit 22 is positioned on the innermost side of the sample output unit 23 as shown in FIG. 4A, the barcode readers B31 of the reading sections B1 and B2 read the rack ID of the sample rack L and the sample IDs of sample containers T as shown in FIG. 4B. At this time, due to the movement of the reading sections B1 and B2 in the rightward direction (X-axis negative direction), the barcode readers 31 of the reading sections B1 and B2 read the barcodes in order from the left. By the barcode reader 31 of the reading section B1, the rack ID of the sample rack L, and the sample IDs of the sample containers T which are held in the left-half portion (holding sections 1 to 5) of the sample rack L are read, and by the barcode reader 31 of the reading section B2, the rack IDs of the sample containers T which are held in the right-half portion (holding sections 6 to 10) of the sample rack L are read.

Here, as shown in FIG. 2A, the barcode portion of the barcode label BL1 adhered to the sample container T is limited to a part of the outer circumference around the Z-axis. For this reason, even when the sample container T is rotated, when a positional relationship in which the barcode portion of the sample container T and the barcode reader B31 are opposed to each other is not achieved during the reading operation of the barcode reader B31, the barcode is not read by the barcode reader B31.

Accordingly, in this embodiment, during the period in which the barcode of a sample container T is read, the sample container T is rotated once. Accordingly, the barcode portion of the sample container T necessarily meets the barcode reader B31 and the barcode is read.

FIG. 4C is a view showing the barcode unit C. As shown in FIG. 4C, the barcode unit C includes two rollers C11, a roller C21, a base C30, and a barcode reader C31. The base C30 and the barcode reader C31 are fixed to the inside of the measurement unit 41. In this case, the sample ID of a sample container T which is positioned in front of the barcode reader C31 (in the X-axis negative direction) is read as in the barcode unit B. That is, the two rollers C11 are moved in the rightward direction (in the X-axis negative direction) and the roller C21 is rotated around the Z-axis, and thus the sample container T is rotated. In this state, the barcode label BL1 of the sample container T is read multiple times by the barcode reader C31.

FIG. 4D is a view showing the barcode unit D. As shown in FIG. 4D, the barcode unit D includes two rollers D11, a roller D21, a base D30, and a barcode reader D31. The base D30 and the barcode reader D31 are fixed near the transport line L1 of the sample transport unit 5. A mechanism for driving the rollers D11 and D21 is disposed immediately in front of a sample rack L in FIG. 4D.

In this case also, the sample ID of a sample container T which is positioned in front of the barcode reader D31 (in the Y-axis positive direction) is read as in the above-described barcode unit B. That is, the two rollers D11 are moved in the downward direction (in the Y-axis positive direction) and the roller D21 is rotated around the Z-axis, and thus the sample container T is rotated. In this state, the barcode label BL1 of the sample container T is read multiple times by the barcode reader D31.

FIG. 5 shows the configuration of the barcode unit B in detail. Since the barcode units C and D have almost the same configuration as that of the barcode unit B, only the barcode unit B will be described hereinafter.

FIG. 5A is a plan view when the rollers B11 and B21 and the surroundings thereof are viewed from the upper side. FIG. 5B is a side view when the barcode unit B is viewed from the left side (in the X-axis negative direction). FIG. 5C is a side view when support sections B33 and B34 and the surroundings thereof are viewed from the front (in the Y-axis negative direction).

Referring to FIGS. 5A and 5B, two rollers B11 and a douser B15 are mounted on a support member B10. Pulleys B13a and B13b, a stepping motor B14, and a sensor B16 are mounted on the base B30. In addition, a flange section B10a is formed in the support member B10. The support member B10 is supported so as to be moved in the Z-axis direction by a guide (not shown) which is installed in the base B30 and extends in the Y-axis direction.

The two rollers B11 are supported so as to be rotated around the Z-axis by the support member B10. A belt B12 runs on the pulleys B13a and B13b.

The pulley B13a is installed in the shaft of the stepping motor B14 so as to be rotated around the Z-axis and the pulley B13b is installed in the base B30 so as to be rotated around the Z-axis. The flange section B10a is fixed to the belt B12.

The douser B15 is a flat plate having a plane perpendicular to the X-axis and is installed on the lower surface of the support member B10. The sensor B16 is a transmission sensor and is composed of a light-emitting section B16a and a light-receiving section B16b. The light-emitting section B16a and the light-receiving section B16b are installed on the base B30 so as to receive the light emitted from the light-emitting section B16a by the light-receiving section B16b and to be opposed to each other in the X-axis direction. In the case in which a sample container T is not held in the holding section in a sample rack L which is positioned in front of the barcode reader B31, when the support member B10 is moved forward, the douser B15 is positioned between the light-emitting section B16a and the light-receiving section B16b.

When a mechanism for driving the support member B10 is configured in this way, the belt B12 moves around the pulleys B13a and B13b due to the driving of the stepping motor B14. Accordingly, with the two rollers B11, the support member B10 moves in the Y-axis direction on the base B30. In addition, with a signal which is output from the light-receiving section B16b, it is found whether or not the support member B10 is moved forward up to a position where it is determined that there is no sample container T.

Referring to FIG. 5B, the roller B21, a shaft B22 and a pulley B24b are mounted on a support member B20. The support member B20 is screwed to the base B30.

The roller B21 has a hole formed therethrough in the Z-axis direction. The shaft B22 passes through this hole and supports the roller B21. In addition, both ends of the shaft B22 are supported by the support member B20 so as to be rotated around the Z-axis. A belt B23 runs on the pulleys B24a and B24b. The pulley B24a is installed in the shaft of a stepping motor B25 so as to be rotated around the Z-axis and the pulley B24b is installed in the support member B20 and the support shaft B22 so as to be rotated around the Z-axis. The stepping motor B25 is installed in the base B30.

When a mechanism for driving the roller B21 is configured in this way, the belt B23 moves around the pulleys B24a and B24b due to the driving of the stepping motor B25. Accordingly, the shaft B22 and the roller B21 are rotated around the Z-axis.

Referring to FIGS. 5B and 5C, the barcode reader B31, a receiving section B32, two belts B35, two pulleys B36a, two pulleys B36b, and two stepping motors B37 are disposed on the lower surface of the base B30 (surface in the Z-axis negative direction).

The barcode reader B31 and the receiving section B32 are installed on the lower surface of the base B30. The support sections B33 and B34 are installed on the lower surfaces of the bases B30 of the reading sections B1 and B2, respectively. A guide 23c extending in the X-axis direction is installed on the upper surface of a support section 23b which is installed on the innermost side (end in the Y-axis negative direction) of the sample output unit 23. The base B30 is supported so as to be moved in the X-axis direction on the guide 23c via the receiving section B32.

The two pulleys B36a and the two pulleys B36b are installed on the side surface of the support section 23b of the sample output unit 23 in the Y-axis negative direction so as to be rotated around the Y-axis. As shown in FIG. 5C, the two belts B35 run on the pulleys B36a and B36b. The support sections B33 and B34 are fixed to the upper and lower belts B35, respectively. The two stepping motors B37 are installed in the support section 23b and are connected to the two pulleys B36a.

When a mechanism for driving the base B30 is configured in this way, the two belts B35 moves around the pulleys B36a and B36b due to the driving of the two stepping motors B37. Accordingly, the support sections B33 and B34 are moved in the X-axis direction and thus the bases B30 of the reading sections B1 and B2 are moved individually in the X-axis direction.

Figure 6:
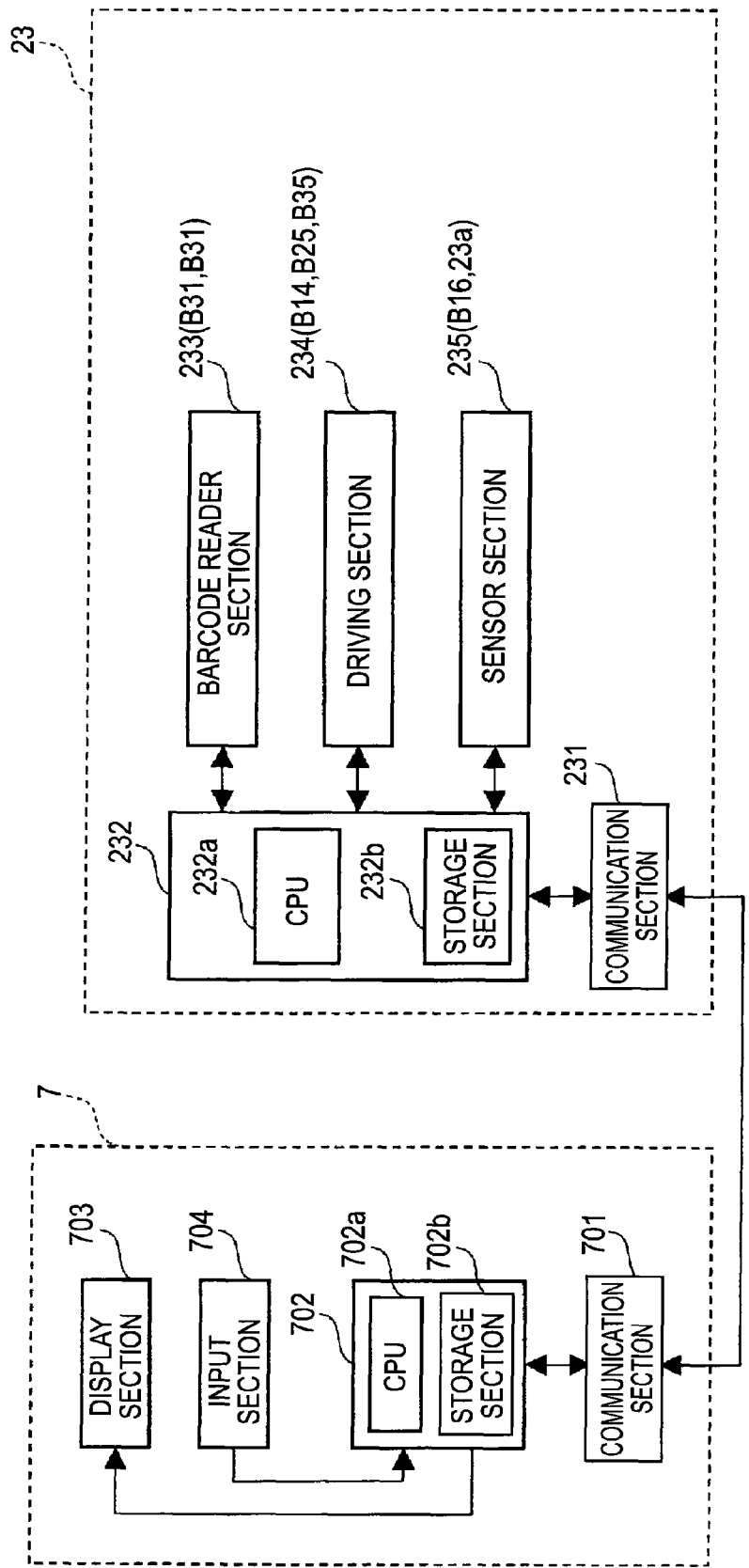
FIG. 6 is a diagram showing the functional configurations of a sample output unit and a transport controller according to the embodiment.

FIG. 6 is a diagram showing the functional configurations of the sample output unit 23 and the transport controller 7.

In the sample output unit 23, a communication section 231 performs data communication with the transport controller 7. A controller 232 has a storage section 232b including a CPU 232a, a ROM, a RAM, a hard disk and the like. The CPU 232a controls sections in accordance with a computer program which is stored in the storage section 232b.

The CPU 232a obtains the sample ID of a sample which is contained in a sample container T on the basis of the reading result read by a barcode reader section 233. The process of obtaining a sample ID will be described later in detail with reference to FIGS. 10 to 12.

The barcode reader section 233 includes the two barcode readers B31 which are included in the reading sections B1 and B2. The reading result which is output from the barcode reader section B233 is output to the controller 232.

A driving section 234 includes the stepping motors B14, B25 and B37 which are included in the reading sections B1 and B2 and the stepping motors in other driving mechanisms. In addition, the driving section 234 includes a rotary encoder which is disposed in each stepping motor. The rotary encoder outputs a pulse signal corresponding to the rotation amount of the stepping motor.

A sensor section 235 includes the sensors B16 which are included in the reading sections B1 and B2 and the sensor 23a which is disposed in the sample output unit 23. A detection signal of the sensor section 235 is output to the controller 232.

In the transport controller 7, a communication section 701 performs data communication with the sample recovery unit 21, the sample insertion unit 22, the three sample transport units 3, and the sample transport unit 5 other than the sample output unit 23. A controller 702 has a storage section 702b including a CPU 702a, a ROM, a RAM, a hard disk and the like. The CPU 702a controls sections in accordance with a computer program which is stored in the storage section 702b. A display section 703 has a display device such as a monitor. An input section 704 has a mouse or a keyboard.

Figure 7:
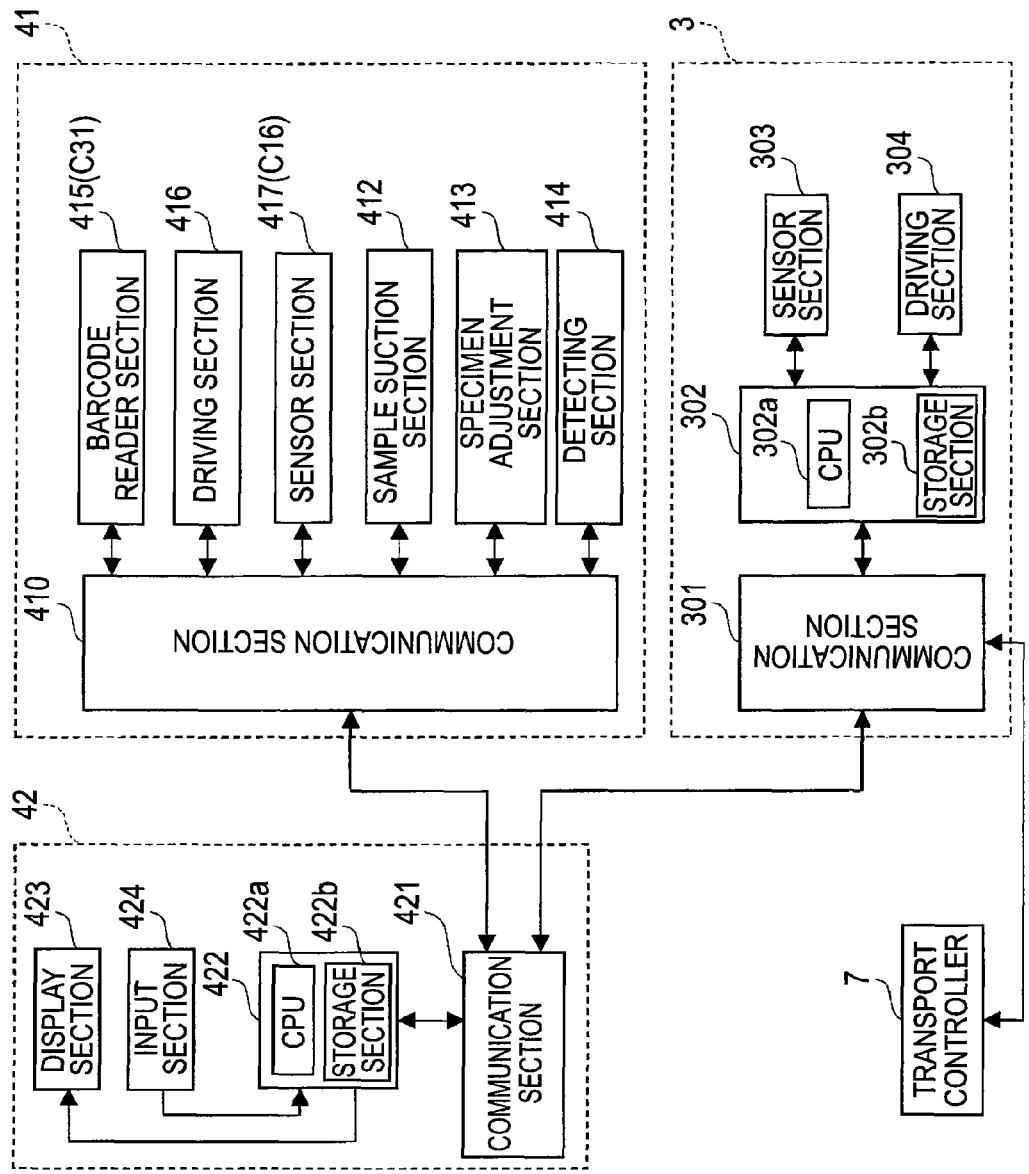
FIG. 7 is a diagram showing the functional configurations of a sample transport unit, the measurement unit and an information processing unit according to the embodiment.

FIG. 7 is a diagram showing the functional configurations of the sample transport unit 3, the measurement unit 41, and the information processing unit 42. In FIG. 7, for the sake of convenience, only one sample transport unit 3 and only one measurement unit 41 are shown. However, the other sample transport units 3 and the other measurement units 41 also have the same configuration.

In the sample transport unit 3, a communication section 301 performs data communication between the transport controller 7 and the information processing unit 42. A controller 302 has a storage section 302b including a CPU 302a, a ROM, a RAM, a hard disk and the like. The CPU 302a controls sections in accordance with a computer program which is stored in the storage section 302b. A sensor section 303 includes a sensor disposed in the sample transport unit 3 and a driving section 304 includes a driving mechanism for the sample transport unit 3.

The sections in the measurement unit 41 are controlled by a controller 422 of the information processing unit 42. The controller 422 of the information processing unit 42 performs data communication with the sections in the measurement unit 41 via communication sections 421 and 410 and controls the sections in the measurement unit 41.

The measurement unit 41 includes a barcode reader section 415, a driving section 416, and a sensor section 417 in addition to the sample suction section 412, the specimen adjustment section 413, and the detecting section 414 shown in FIG. 3. The barcode reader section 415 includes a barcode reader C31. The reading result which is output from the barcode reader section 415 is transmitted to the controller 422 of the information processing unit 42 via the communication section 410. The driving section 416 includes a stepping motor which is included in the barcode unit C and a rotary encoder which is disposed in the stepping motor. The sensor section 417 includes a sensor C16 which is included in the barcode unit C. The sensor C16 has the same function as that of the sensor B16 of the barcode unit B and a detection signal of the sensor section 417 is transmitted to the controller 422 of the information processing unit 42 via the communication section 410.

In the information processing unit 42, the communication section 421 performs data communication between the communication section 301 of the sample transport unit 3 and the communication section 410 of the measurement unit 41. The controller 422 has a storage section 422b including a CPU 422a, a ROM, a RAM, a hard disk and the like. The CPU 422a controls the sections in the information processing unit 42 and the sections in the measurement unit 41 in accordance with a computer program which is stored in the storage section 422b. In addition, the CPU 422a performs blood analysis on the basis of the measurement result (particle data) which is received from the measurement unit 41 and displays the analysis result on a display section 423. Such analysis result is transmitted to the transport controller 7 via the sample transport unit 3. Further, the CPU 422a inquires of the host computer 8 for a measurement order via the communication section 421. In addition, the CPU 422a obtains the sample ID of a sample which is contained in a sample container T on the basis of the reading result from the barcode reader section 415 as in the CPU 232a of the sample output unit 23.

The display section 422 and an input section 424 have the same configurations as those of the display section 703 and the input section 704 of the transport controller 7.

FIG. 8 is a diagram showing the functional configurations of the sample transport unit 5 and the smear preparation apparatus 6.

In the sample transport unit 5, a communication section 501 performs data communication between the smear preparation apparatus 6 and the transport controller 7. A controller 502 has a storage section 502b including a CPU 502a, a ROM, a RAM, a hard disk and the like. The CPU 502a controls the sections in accordance with a computer program which is stored in the storage section 502b. In addition, the CPU 502a obtains the sample ID of a sample which is contained in a sample container T on the basis of the reading result from a barcode reader section 503 as in the CPU 232a of the sample output unit 23. A driving section 504 includes a stepping motor which is included in the barcode unit D and the stepping motors in other driving mechanisms. In addition, the driving section 504 includes rotary encoders which are disposed in the stepping motors, respectively. A sensor section 505 includes a sensor D16 which is included in the barcode unit D. The sensor D16 has the same function as that of the sensor B16 of the barcode unit B.

In the smear preparation apparatus 6, the communication section 301 performs data communication with the sample transport unit 5. A controller 602 has a storage section 602b including a CPU 602a, a ROM, a RAM, a hard disk and the like. The CPU 602a controls the sections in accordance with a computer program which is stored in the storage section 602b. A sensor section 603 includes a sensor which is disposed in the sample transport unit 5.

In the above-described configuration, each of the barcode units B, C, and D of the sample output unit 23, the measurement unit 41, and the sample transport unit 5 reads the barcode label BL1 multiple times from a rotating container T as in the above description based on FIGS. 4A to 4D.

Here, in some cases, the state of the barcode label BL1 which is adhered to the sample container T may be as shown in FIGS. 9A and 9B. In this case, there is concern that a correct sample ID may not be read by the barcode unit B, C, or D.

FIG. 9A is a diagram showing the state in which on an old barcode label BL1 which is adhered to a sample container T, another new barcode label BL1 is adhered. When the barcode unit B, C, or D performs barcode reading on this sample container T as described above, a different sample ID may be read. That is, when the reading is executed at a position R1, the correct sample ID is read from the upper barcode label BL1. However, when the reading is executed at a position R2, the wrong sample ID is read from the lower barcode label BL1.

FIG. 9B is a diagram showing the state in which a barcode label BL1 which is adhered to a sample container T is slanted. When the barcode unit B, C, or D performs barcode reading on this sample container T as described above, a wrong sample ID may be read or the reading may fail. That is, when the reading is executed at a position R3, the correct sample ID is read from the barcode label BL1. However, when the reading is executed at a position R4, the wrong sample ID may be read or the reading may fail due to the cancellation of significant digits occurring in the read result.

Accordingly, as described above, when a barcode is read multiple times from a rotating sample container T, a process for properly determining which ID is to be employed as a true value among the read plural sample IDs is required. In this embodiment, even when the barcode label BL1 is adhered to the sample container T in the state shown in FIG. 9A or 9B, a process for properly determining a sample ID to be employed as a true value among obtained plural sample IDs is performed.

Figure 10:
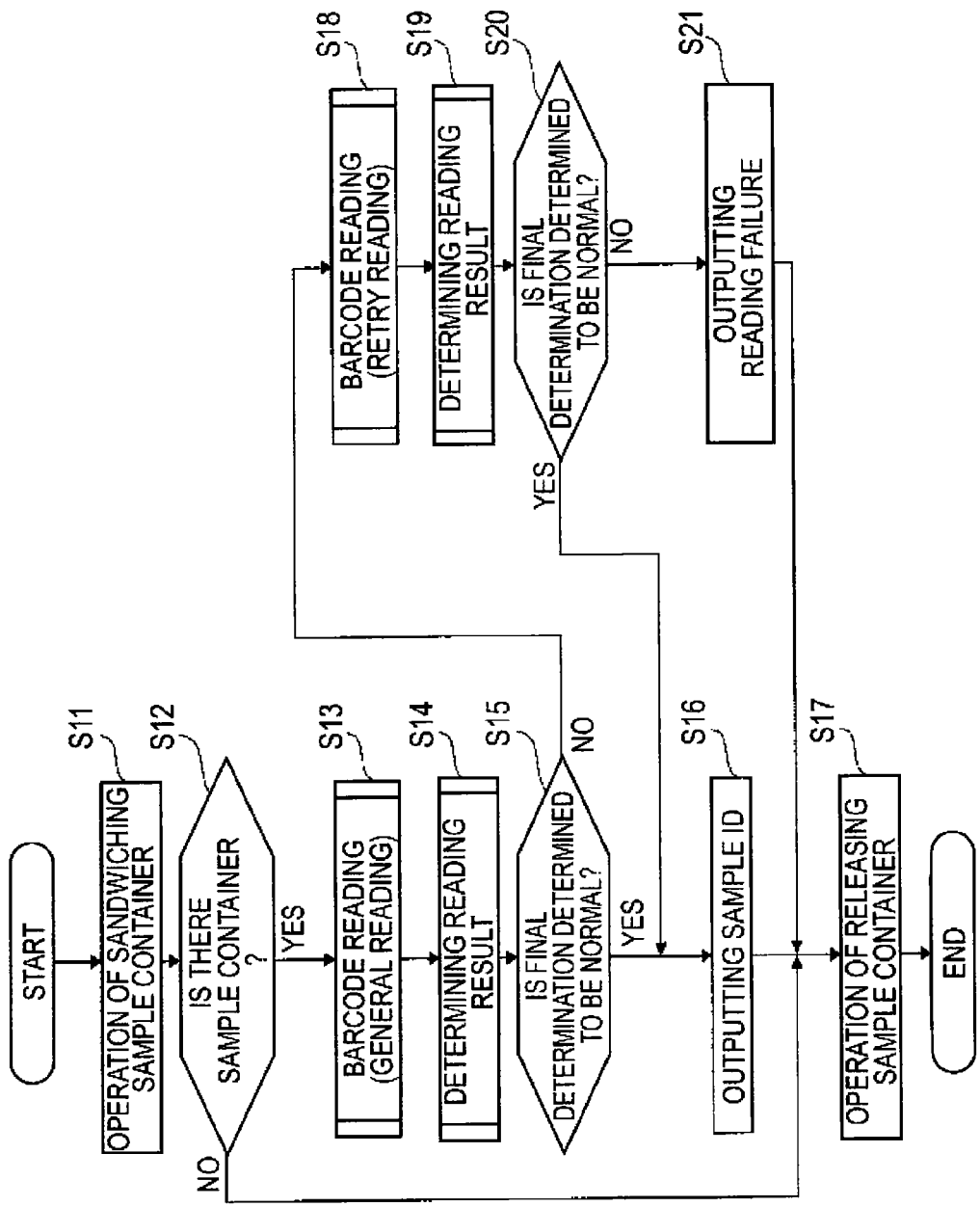
FIG. 10 is a flowchart showing a process of determining the sample ID of a sample container according to the embodiment.

FIG. 10 is a flowchart showing a process of determining the sample ID of a sample container T. Since almost the same process is performed in the barcode units B, C and D, only the processing flowchart related to the barcode unit B will be described hereinafter.

When the barcode reader B31 of the reading section B1 or B2 is positioned in front of a holding section in a sample rack L in which the reading is to be executed, the CPU 232a of the sample output unit 23 drives the stepping motor B14 and performs an operation of sandwiching a sample container T (S11). That is, the support member B10 is moved forward so that the sample container T is sandwiched between the two rollers B11.

When the CPU 232a determines that there is no sample container T in this holding section by an output signal of the light-receiving section B16b (S12: NO), the process proceeds to S17. When the CPU 232a determines that there is a sample container T in this holding section (S12: YES), a "barcode reading" process is performed as general reading (S13) and a "reading result determination" process is performed on the basis of the reading result obtained in S13 (S14). The "barcode reading" process and the "reading result determination" process will be described later with reference to FIGS. 11 and 12, respectively.

Next, when determining a final determination to be described later to be normal by the "reading result determination" process of S14 (S15: YES), the CPU 232a outputs the sample ID obtained by the "reading result determination" process of S14 to the subsequent circuit (S16). That is, in this case, the sample ID determined to be normal is transmitted to the transport controller 7.

On the other hand, when determining the final determination to be wrong (failed) by the "reading result determination" process of S14 (S15: NO), the sample ID of the sample container T is re-read. That is, the "barcode reading" process is performed as a retry reading on this sample container T (S18) and the "reading result determination" process is performed on the basis of the reading result obtained in S18 (S19).

Next, when determining that the final determination is determined to be normal by the "reading result determination" process of S19 (S20: YES), the CPU 232a outputs the sample ID obtained by the "reading result determination" process of S19 to the subsequent circuit (transport controller 7) (S16). On the other hand, when determining that the final determination is determined to be wrong (failed) by the "reading result determination" process of S19 (S20: NO), the fact that the reading has failed is output to the subsequent circuit (transport controller 7) (S21).

After that, the CPU 232a drives the stepping motor B14 and performs an operation of releasing this sample container T (S17). That is, the support member B10 is moved backward so that the rollers B11 are moved backward from the position at which the sample container T is sandwiched between the rollers B11.

FIG. 11A is a flowchart showing the "barcode reading" process. FIG. 11B is a flowchart showing a "timeout counting" process which is performed concurrently with the "barcode reading" process of FIG. 11A.

Referring to FIG. 11A, the CPU 232a of the sample output unit 23 rotates the sample container T, which is sandwiched in S11 of FIG. 10, by driving the stepping motor B25 and thus rotating the roller B21 at a constant rotation speed (S101). At this time, in general reading, the sample container T is rotated counterclockwise at a predetermined rotation speed. In addition, in the case of the retry reading, the sample container T is rotated clockwise at half the rotation speed of the general reading.

Accordingly, in the general reading, even when the barcode label BL1 is partially peeled and hung in the holding section in the sample rack L and thus it becomes difficult to rotate the sample container T, the sample container T is smoothly rotated in the retry reading. That is, in the retry reading, since the sample container T is rotated in the reverse direction to the direction in the general reading, the snagging of the barcode label BL1 in the holding section is solved and a possibility of proper reading is increased.

Here, when the rotation of the sample container T is started, the CPU 232a starts the "timeout counting" process shown in FIG. 11B and starts counting of an elapsed time T1 (S111).

When the rotation of the sample container T is started in S101 of FIG. 11A, the CPU 232a sets a variable n indicating the number of times of obtaining the result to 1 (S102). The variable n is stored in the storage section 232b of the sample output unit 23. Next, the CPU 232a issues a reading instruction to the barcode reader B31 (S104) and starts the counting of an elapsed time T2 after the issuing of this reading instruction (S104).

Next, when determining that the elapsed time T2 is shorter than a predetermined time Tw (S105: YES), the CPU 232a sets to standby the process until the reading result is received from the barcode reader B31. That is, when the CPU 232a does not receive the reading result (S106: NO), the process returns to S105. When the CPU 232a receives the reading result (S106), the CPU stores this result as the n-th result in the storage section 232b (S107). After that, 1 is added to the value of the variable n (S108) and the process returns to S103. On the other hand, when the CPU 232a determines that the elapsed time T2 is equal to or longer than the predetermined time Tw (S105: NO), the process returns to S103. In this way, the storage of the reading result is repeatedly performed.

Concurrently with this, the elapsed time T1 is monitored by the process of FIG. 11B. When determining that the elapsed time T1 is shorter than a predetermined time Tout (S112: YES), the CPU 232a sets to standby the process. When determining that the elapsed time T1 is equal to or longer than the predetermined time Tout (S112: NO), in S107 of FIG. 11A, the CPU 232a adds the timeout to the end of the reading results which have been stored (S113) and terminates the processes of FIGS. 11A and 11B. When the process is terminated in this way, a decrease in process efficiency is suppressed without endless continuation of the reading operation on one sample container T.

The predetermined time Tout is set to a time which is required to rotate the sample container T once. That is, in the cases of the general reading and the retry reading, when the sample container T is rotated for the predetermined time Tout on the basis of the set rotation speed of the sample container T, the sample container T is rotated once. In addition to the rotation of the sample container T at a constant rotation speed, when the barcode is repeatedly read for a time necessary for the rotation of the sample container T by a predetermined angle (one rotation, in this embodiment), the barcode can be read in the whole range of the rotation angle set in advance. Further, there is no need to provide a mechanism (for example, encoder) for detecting the fact that the sample container has been rotated by the predetermined angle since the process is completed at the time when the predetermined time necessary for the rotation of the sample container T by the predetermined angle has elapsed.

According to the processes of FIGS. 11A and 11B, while the sample container T is rotated once, the barcode is read at an interval of the predetermined time Tw at the longest, and as great a number of reading results as possible are stored in the storage section 232b.

The reading results stored in S107 and S113 are stored in, for example, the storage section 232b, as shown in the reading result item in FIG. 13.

In the reading result item in FIG. 13, examples of the reading results when the barcodes of ten sample containers T with Sample Nos. 1 to 10 are read are shown, respectively. 'AAA', 'BBB', and 'CCC' indicate sample IDs of the sample containers T in which reading has been performed. "T/O" is a symbol indicating the timeout in S113 of FIG. 11B. "NG" is a symbol indicating that the CPU 232a has received an error from the barcode reader B31 in S106 of FIG. 11A. Such an error is generated when an error is detected by a check digit in the barcode reader B31.

In this way, the stored reading results are determined in S14 and S19 of FIG. 10.

FIG. 12 is a flowchart showing the "reading result determination" process. In the following number of the reading results, "NG" and "T/O" shown in FIG. 13 are not included.

When determining that the number of the reading results related to the sample container T is equal to or less than 1 (S201: YES), the CPU 232a views the determination (hereinafter, referred to as the "final determination") of the reading results of this sample container T as a failure (S202) and the process ends. On the other hand, when determining that the number of the reading results related to the sample container T is equal to or greater than 2 (S201: NO), the CPU 232a determines whether or not the number of the reading results is equal to or greater than 2 and equal to or less than 4 (S203). When it is determined that the number of the reading results is equal to or greater than 2 and equal to or less than 4 (S203: YES), the process proceeds to S204, and when it is determined that the number of the reading results is equal to or less than 5 (S203: NO), the process proceeds to S207.

In S204, the CPU 232a determines whether the sample ID of the first reading result matches the sample ID of the second reading result. When the sample ID of the first reading result matches the sample ID of the second reading result (S204: YES), the final determination is viewed as normal (S205), the matching sample ID is regarded as the sample ID of this sample container T (S206) and the process ends. On the other hand, when the sample ID of the first reading result does not match the sample ID of the second reading result (S204: NO), the final determination is viewed as a failure (S202) and the process ends.

In S207, the CPU 232a determines whether the number of the sample IDs occupying a majority of the reading results is equal to or greater than a predetermined ratio R to the total number of the reading results (S207). When the number of the sample IDs is equal to or greater than the predetermined ratio R (S207: YES), the final determination is viewed as normal (S208), the sample ID occupying the majority is regarded as the sample ID of this sample container T (S209) and the process ends. On the other hand, when the ratio of the sample ID occupying the majority is less than the predetermined ratio R (S207: NO), the CPU 232a views the final determination as a failure (S202) and the process ends. The predetermined ratio R which is used in S207 is larger than 50%.

The final determination related to the Sample Nos. 1 to 10 exemplified in FIG. 13 are shown in the final determination item in FIG. 13. In the example shown in FIG. 13, the predetermined ratio R is set to 60%.

Referring to FIG. 13, when the number of the reading results is equal to or less than 1, the final determination is viewed as a failure as shown in the Sample Nos. 1 and 2. When the number of the reading results is in the range of 2 to 4, the sample ID of the first reading result matches the sample ID of the second reading result in the Sample Nos. 3 to 5, and thus the final determination is viewed as normal. In the Sample No. 6, the sample ID of the first reading result does not match the sample ID of the second reading result, and thus the final determination is viewed as a failure. When the number of the reading results is equal to or greater than 5, the ratio of the sample ID occupying the majority is equal to or greater than 60% in the Sample Nos. 7 and 9, and thus the final determination is viewed as normal. The ratio of the sample ID occupying the majority is less than 60% in the Sample Nos. 8 and 10, and thus the final determination is viewed as a failure.

As described above, according to this embodiment, even when the barcode label BL1 is adhered over as shown in FIG. 9A or the barcode label BL1 is adhered to be slanted as shown in FIG. 9B, a high-accuracy sample ID can be obtained.

That is, when the number of the reading results is equal to or less than 1, the reading result is viewed as a failure. Accordingly, it is possible to avoid using a sample ID, which is read only once and of which the reading result may not be correct, as a true value.

In addition, when the number of the reading results is equal to or greater than 5 and the ratio of the sample ID occupying the majority is equal to or greater than the predetermined ratio R, this sample ID is employed as a true value. Accordingly, as described with reference to FIG. 9, even when a wrong sample ID is read, a correct sample ID read over the large area is employed as a true value, and thus the accuracy of the finally obtained sample ID can be increased.

In addition, when the number of the reading results is equal to or greater than 2 and equal to or less than 4 and the sample ID of the first reading result matches the sample ID of the second reading result, this sample ID is employed as a true value. Accordingly, even when the number of the reading results of the sample ID occupying the majority is small and thus it is difficult to determine that the above sample ID occupies the majority, the accuracy of the sample ID which is employed as a true value can be maintained.

In addition, according to this embodiment, reading the barcode of a sample container T is performed over the whole range during one rotation of the sample container T. Accordingly, a new barcode is necessarily read over a large area regardless of how the barcode label BL1 is adhered to the side surface of the sample container T. Accordingly, the accuracy of the obtained sample ID can be increased.

In addition, according to this embodiment, when it is determined that the final determination is not normal on the basis of the reading results obtained by the general reading, the retry reading is performed. Accordingly, even when a proper sample ID is not obtained through the general reading, it can be expected that a proper sample ID is obtained by the retry reading. In addition, during the retry reading, since the sample container T is rotated in the reverse direction, a possibility of obtaining a proper sample ID can be increased as described above.

As described above, the embodiment of the invention has been described, but is not limited thereto.

For example, in the above-described embodiment, blood is exemplified as a measurement target, but urine may also be a measurement target. That is, the invention can also be applied to a sample processing apparatus which examines urine, and further, can also be applied to a clinical sample examination apparatus which examines other clinical samples.

In addition, in the above-described embodiment, Tw, which is used in the "barcode reading" process of FIG. 11A, Tout, which is used in the "timeout counting" process of FIG. 11B, the number of the reading results, which is used in the determination in S201 and S203 of FIG. 12, and the predetermined ratio R, which is used in the determination in S207 of FIG. 12, are set as fixed values, respectively, but they may be set by a user. In addition, the barcode type (for example, CODE128, NW-7, ITF, CODE39, JAN and the like) which can be read by the barcode unit B may be set by a user.

In this case, for example, the settings of the barcode units B and D are set via the input section 704 of the transport controller 7 and the settings of the barcode unit C are set via the input section 424 of the information processing unit 42. In the cases of the barcode units B and D, these set values are transmitted via the communication sections and are stored in the storage section 232b of the sample output unit 23 and the storage section 502b of the sample transport unit 5, respectively. In the case of the barcode unit C, the setting values are stored in the storage section 422b of the information processing unit 42.

In addition, in the above-described embodiment, the barcode of a sample container T is read during one rotation of this sample container T, but the invention is not limited thereto. The barcode of a sample container T may be read during ¾ or ½ rotation of this sample container T. Accordingly, the unnecessary reading action can be suppressed.

FIG. 14 schematically shows a ratio of a barcode portion (barcode range) in the barcode label BL1 to the outer circumference of a sample container T and a ratio of a reading range of the barcode reader when the sample container T is viewed from the upper side. When a barcode label BL1 is adhered to a sample container T having a standard outer circumferential length, a ratio of the barcode range is about 50% of the outer circumferential length.

FIG. 14A is a diagram showing the case in which the barcode reader reading is performed in the range of 75% of the outer circumference when the barcode range is 50% of the outer circumference. In this case, the remaining range (50%)

excluding the barcode range is included in the reading range (75%) of the barcode reader, but at least half the barcode range is always read. Accordingly, when the reading results of this case are subjected to the determination process of FIG. 12, sample IDs are obtained on the basis of the reading results properly read over the large area, and thus the accuracy of a sample ID which is finally obtained can be increased.

FIG. 14B is a diagram showing the case in which the barcode reader reading is performed in the range of 50% of the outer circumference when the barcode range is 50% of the outer circumference of a sample container T. In this case, when the reading range (50%) of the barcode reader is the remaining range (50%) excluding the barcode range, the barcode cannot be read. However, actually, since the barcode reading is performed on a sample container T randomly installed, the case in which the reading range of the barcode is outside the barcode range is very rare. Accordingly, even when the barcode reading is performed on a sample container T in this way, in most cases, the barcode reading is performed over a certain amount of range. Therefore, in this case also, a proper sample ID can be obtained with high probability by performing the determination process of FIG. 12.

When a barcode label BL1 is adhered to a fine sample container T as shown in FIG. 14C, the barcode can be properly read in the large range even when the reading range of the barcode reader is about 50% of the outer circumference.

FIG. 14C shows the case in which the barcode reading is performed in the range of 50% of the outer circumference when the barcode range occupies 75% of the outer circumference of a sample container T. In this case, at least ⅓ of the barcode is always read. Accordingly, when the reading results of this case are subjected to the determination process of FIG. 12, sample IDs are obtained on the basis of the reading results properly read over the large area, and thus the accuracy of a sample ID which is finally obtained can be increased.

The rotation angle of a rotating sample container may not necessarily correspond to the barcode reading range.

The reading range with respect to the outer circumference of the sample container T may be manually set. Accordingly, when a ratio of the barcode range to the outer circumference of the sample container T is changed, such as when the diameter of the sample container T is changed, the reading range can be appropriately adjusted so that a sufficient area of the barcode range is read in accordance with the ratio. Therefore, the unnecessary rotation action is suppressed and the barcode can be properly read.

In addition, in the above-described embodiment, a sample container T is rotated once in the general reading and the retry reading, but the invention is not limited thereto. The rotation angle of a sample container T may be different in the general reading and the retry reading. For example, in the general reading, the rotation angle may be 50% of the whole circumference, and in the retry reading, the rotation angle may be 75% of the whole circumference. Accordingly, a time required for the general reading can be shortened, and even when the barcode reading is not performed in the general reading, the barcode reading can be securely performed in the retry reading.

In addition, in the "reading result determination" process (FIG. 12) according to the above-described embodiment, it is determined whether the number of the reading results is equal to or less than 1 in S201 and it is determined whether the number of the reading results is equal to or less than 4 in S203 when the determination result is NO in S201. However, the invention is not limited thereto and the settings may be appropriately set, respectively.

In the processing flow of FIG. 12, the maximum number of the reading results when the determination result is YES in S203 is 4. However, when the step S203 is changed so that the maximum number of the reading results at this time is equal to or greater than 5, the step S204 can be changed, for example, as follows. That is, when there are units of two or more continuous times of sample IDs in a plurality of sample IDs read, (1) the sample ID of the unit in which the number of continuation of the sample IDs is highest is set to a final sample ID, and (2) when the number of the units in which the number of continuation of the sample IDs is highest is more than one, the sample ID of the unit read firstly is set to a final sample ID.

In this case, when there are no units of two or more continuous times of sample IDs, the final determination is viewed as a failure (S202).

In addition, in the above-described embodiment, on the basis of the sample IDs obtained by the barcode units B, C, and D, the CPU 232a, the CPU 422a, and the CPU 502a determine sample IDs which are true values, respectively. However, the invention is not limited thereto and the determination may be carried out in the barcode units B, C, and D. In this case, in the barcode units B, C, and D, a CPU and a storage section are provided and a sample ID which is a true value is determined by this CPU.

Further, in the above-described embodiment, a sample container T is rotated during the reading of the barcode label BL1. However, a sample container T may be fixed and the barcode readers B31, C31, and D31 may be rotated in the circumferential direction of the sample container T.

In addition, in the above-described embodiment, the configuration has been provided in which the barcode reading of the reading section is stopped when a time required to rotate a sample container by a predetermined angle has elapsed, but the invention is not limited to this configuration. For example, a configuration may be provided in which an encoder is provided which detects the rotation amount of a sample container and the barcode reading is stopped when the encoder detects that the sample container has been rotated by a predetermined angle.

Various modifications may be properly made in the embodiments of the invention within the scope of the technical idea shown in the claims.

What is claimed is:
1. A sample analyzer comprising:
   a measurement unit for measuring a sample contained in a sample container;
   a barcode reader for reading a barcode adhered to the sample container;
   a rotating section for rotating the sample container relative to the barcode reader so that a position at which the reading is performed by the barcode reader moves in a circumferential direction of the sample container; and
   a controller which executes operations, the operations comprising:
      controlling the rotating section and the barcode reader so that the barcode reader repeatedly reads the barcode to obtain one or more barcode reading results over the range of a predetermined rotation angle; and
      identifying the sample based on the number of barcode reading results obtained for the sample container over a predetermined time period, wherein identifying the sample comprises:
         in response to a determination that the number of barcode reading results is greater than or equal to a predetermined number:

identifying a majority barcode reading result corresponding to the barcode reading result that appears most often among the barcode reading results;

determining whether a ratio of the number of barcode reading results matching the majority barcode reading result over the total number of barcode reading results is greater than or equal to a predetermined ratio; and in response to a determination that the ratio is greater than or equal to the predetermined ratio, identifying the sample by the majority barcode reading result.

2. The sample analyzer according to claim 1, wherein the controller causes the barcode reader to repeatedly read the barcode at least while the sample container is rotated 360 degrees.

3. The sample analyzer according to claim 1, wherein the controller causes the barcode reader to repeatedly read the barcode at least while the sample container is rotated by 180 degrees.

4. The sample analyzer according to claim 1, wherein the controller causes the barcode reader to repeatedly read the barcode at least while the sample container is rotated by 270 degrees.

5. The sample analyzer according to claim 1, wherein when a time required to read the barcode by the barcode reader in the range of the predetermined rotation angle has elapsed, the controller controls rotating section to terminates the rotation and controls the barcode reader to terminates the reading.

6. The sample analyzer according to claim 1, wherein the controller retries the controlling operation and the obtaining operation when a number of the reading results does not satisfy a first threshold.

7. The sample analyzer according to claim 6, wherein when the number of the reading results is equal to or greater than the first threshold and equal to or less than a second threshold, the controller obtains the identification information on the basis of one reading result which is continuously read.

8. The sample analyzer according to claim 1, wherein the controller retries rotating the sample and reading the bar code when the controller fails to obtain identification information.

9. The sample analyzer according to claim 8, wherein the controller controls the rotating section so that the rotation is performed in a direction reverse against a direction of an initial rotation when the controller retries rotating the sample.

10. The sample analyzer according to claim 8, wherein the controller controls the rotating section so that the rotation of the retried operation is performed at a speed lower than a rotation speed in an initial rotation.

11. The sample analyzer according to claim 8, wherein the rotating section includes at least three rollers and rotates the sample container by rotating any one of the rollers in a state in which the rollers are brought into contact with the sample container.

12. The sample analyzer according to claim 1, wherein the sample container is a vacuum blood collection tube, and the measurement unit measures blood cells included in blood as a sample which is contained in the vacuum blood collection tube.

13. A method of obtaining sample identification information, the method comprising:

repeatedly reading a barcode adhered to a sample container containing a sample over a range of a predetermined rotation angle by rotating the sample container to obtain one or more barcode reading results; and identifying the sample based on the number of barcode reading results obtained for the sample container over a predetermined time period, wherein identifying the sample comprises:

in response to a determination that the number of barcode reading results is greater than or equal to a predetermined number:

identifying a majority barcode reading result corresponding to the barcode reading result that appears most often among the barcode reading results;

determining whether a ratio of the number of barcode reading results matching the majority barcode reading result over the total number of barcode reading results is greater than or equal to a predetermined ratio; and in response to a determination that the ratio is greater than or equal to the predetermined ratio, identifying the sample by the majority barcode reading result.

14. A sample identification information obtaining apparatus comprising:

a barcode reader for reading a barcode adhered to a sample container;

a rotating section for rotating the sample container relative to the barcode reader so that a position at which the reading is performed by the barcode reader moves in a circumferential direction of the sample container; and a controller which executes operations, the operations comprising:

controlling the rotating section and the barcode reader so that the barcode reader repeatedly reads the barcode to obtain one or more barcode reading results over the range of a predetermined rotation angle; and identifying the sample based on the number of reading results obtained for the sample container over a predetermined time period, wherein identifying the sample comprises:

in response to a determination that the number of barcode read in results is greater than or equal to a first predetermined number and less than or equal to a second predetermined number:

determining whether the first barcode reading result matches the second barcode reading result; and in response to a determination that the first barcode reading result matches the second barcode reading result, identifying the sample by the first barcode reading result; and in response to a determination that the number of barcode read ins results is greater than or equal to a predetermined number:

identifying a majority barcode reading result corresponding to the barcode reading result that appears most often among the barcode reading results;

determining whether a ratio of the number of barcode reading results matching the majority barcode reading result over the total number of barcode reading results is greater than or equal to a predetermined ratio; and in response to a determination that the ratio is greater than or equal to the predetermined ratio, identifying the sample by the majority barcode reading result.

15. A sample analyzer comprising:
a measurement unit for measuring a sample contained in a sample container;
a barcode reader for reading a barcode adhered to the sample container;
a rotating section for rotating the sample container relative to the barcode reader so that a position at which the reading is performed by the barcode reader moves in a circumferential direction of the sample container; and
a controller which executes operations, the operations comprising:
controlling the rotating section and the barcode reader so that the barcode reader repeatedly reads the barcode to obtain one or more barcode reading results over the range of a predetermined rotation angle; and
identifying the sample based on the number of barcode reading results obtained for the sample container over a predetermined time period wherein identifying the sample comprises:
in response to a determination that the number of barcode reading results is greater than or equal to a first predetermined number and less than or equal to a second predetermined number:
determining whether the first barcode reading result matches the second barcode reading result; and
in response to a determination that the first barcode reading result matches the second barcode reading result, identifying the sample by the first barcode reading result.

16. A method of obtaining sample identification information, comprising:
repeatedly reading a barcode adhered to a sample container containing a sample over a range of a predetermined rotation angle by rotating the sample container to obtain one or more barcode reading results; and
identifying the sample based on the number of barcode reading results obtained for the sample container over a predetermined time period, wherein identifying the sample comprises:
in response to a determination that the number of barcode reading results is greater than or equal to a first predetermined number and less than or equal to a second predetermined number:
determining whether the first barcode reading result matches the second barcode reading result; and
in response to a determination that the first barcode reading result matches the second barcode reading result, identifying the sample by the first barcode reading result.

\* \* \* \* \*

UNITED STATES PATENT AND TRADEMARK OFFICE
CERTIFICATE OF CORRECTION

PATENT NO.        : 8,864,030 B2                                   Page 1 of 1
APPLICATION NO.   : 13/039977
DATED             : October 21, 2014
INVENTOR(S)       : Yuichiro Ohmae It is certified that error appears in the above-identified patent and that said Letters Patent is hereby corrected as shown below:

In the Claims

In column 20, claim 14, around line 45, before "results is greater than" replace "read in" with --reading--.

In column 20, claim 14, around line 57, before "results is greater than or" replace "read ins" with --reading--.

Signed and Sealed this
Eighth Day of March, 2016

Michelle K. Lee
*Director of the United States Patent and Trademark Office*